United States Patent [19]

Serino et al.

[11] Patent Number: 4,793,986

[45] Date of Patent: Dec. 27, 1988

[54] MACROMOLECULAR PLATINUM ANTITUMOR COMPOUNDS

[75] Inventors: Anthony J. Serino, West Chester; Geoffrey W. Henson; David A. Schwartz, both of Exton; Donald H. Picker, Merian, all of Pa.

[73] Assignee: Johnson Matthey, Inc., Malvern, Pa.

[21] Appl. No.: 18,715

[22] Filed: Feb. 25, 1987

[51] Int. Cl.$^4$ .............................................. C07F 15/00
[52] U.S. Cl. .................. 424/1.1; 424/85.91; 514/54; 514/58; 436/548; 556/137
[58] Field of Search .................. 514/492, 59; 556/137; 424/1.1, 85; 436/547, 548

[56] References Cited

U.S. PATENT DOCUMENTS

| | | | |
|---|---|---|---|
| 4,385,046 | 5/1983 | Milbrath et al. | 424/1.1 |
| 4,584,392 | 4/1986 | Smith et al. | 556/137 |
| 4,614,811 | 9/1986 | Gandolfi | 556/137 |
| 4,671,958 | 6/1987 | Rodwell et al. | 424/85 |
| 4,673,754 | 6/1987 | Smith et al. | 556/137 |

FOREIGN PATENT DOCUMENTS

| | | |
|---|---|---|
| 0099133 | 1/1984 | European Pat. Off. . |
| 0111388 | 6/1984 | European Pat. Off. ............ 514/492 |
| 0167310 | 1/1986 | European Pat. Off. ............ 514/492 |
| 0190464 | 8/1986 | European Pat. Off. . |

OTHER PUBLICATIONS

*Neoplasma*, 33, 6 (1986) pp. 665–670.
*Inorganica Chimica Acta*, 135 (1987) 27–31.

*Primary Examiner*—John F. Terapane
*Assistant Examiner*—G. Geist
*Attorney, Agent, or Firm*—Cushman, Darby & Cushman

[57] ABSTRACT

A composition comprising a pharmaceutically acceptable polysaccharide carrier which has been chemically activated and then linked to platinum in either a +2 or +4 oxidation state through a bidentate oxygen-containing ligand including an amine group coupled to the activated polysaccharide. The composition may be used to link platinum metal remotely to a monoclonal antibody via the oxygen-containing ligand and the polysaccharide carrier such as dextran. The composition is optionally radiolabeled.

11 Claims, No Drawings

MACROMOLECULAR PLATINUM ANTITUMOR COMPOUNDS

BACKGROUND OF THE INVENTION

1. Technical Field

The present invention relates, in general, to the preparation of platinum-containing compositions to be used for the localization and/or treatment of tumor cells and, in particular, to the preparation of water-soluble platinum-containing macromolecules covalently attached to targeting agents such as monoclonal antibodies, antibody fragments or bioactive peptides.

2. Background Information

The platinum-containing antitumor compound cisplatin is now widely used as a drug for various neoplastic disorders with high efficacy in certain instances. While its exact mode of action is still disputed, it is generally agreed that platinum causes intrastrand crosslinks in DNA which block transcription and effectively halt tumor growth. A major problem with cisplatin as a drug, however, aside from the nausea and vomiting which cause extreme discomfort for the patient, is its severe dose limiting nephrotoxicity. The search for cisplatin analogs with similar antitumor properties, less toxic side effects and a broader range of activity, has produced carboplatin, a diamine malonato platinum complex, which is now used clinically. The decreased nephrotoxicity is believed to be due to the greater in vivo stability of the malonate ligand compared to the chlorides of cisplatin.

To improve the chemotherapeutic activity of platinum complexes, efforts have been made to utilize targeting agents, like monoclonal antibodies, to selectively deliver platinum to tumor cells, thereby avoiding the toxic side effects associated with intravenous or intraperitoneal administration, while achieving a therapeutic dose. See: Heffernan, J. G. et al EPO No. 167,310 and EPO No. 169,645 and Hurwitz, E. et al EPO No. 99,133. The use of biodegradable implants containing cisplatin has been described. See: Drobnik, J. and Stepankova, H. GB No. 2,160,422. In addition, the use of macromolecules to carry a drug to a tumor site has also been suggested. Drug-carrier conjugates prepared to date include mitomycin C-dextran; 5-fluorouridine-dextran and cytosine arabinoside-dextran; methotrexate-poly-L-lysine; daunorubicin-polyglutamate and daunorubicin-dextran; and adriamycin-polyvinyl alcohol. See: Sezaki, H. et al (1980) J. Pharm. Pharmacol. 32, 30–34 and Chem. Pharm. Bull (1985) 33, 2941–2947; Hurwitz, E. et al (1985) J. Med. Chem. 28, 137–140; Rosowsky, A. et al (1985), Mol. Pharm. 27, 141–7; Hurwitz, E. et al (1980) J. Appl. Biochem. 2, 25–35; and Wingard, L. B., Jr. et al (1985) Cancer Res., 45, 3529–3536.

In general, these macromolecular drug conjugates have proven to be less toxic than the monomeric drug while being equally or more effective in killing cancer cells. Of the platinum(II)-containing macromolecules which have been prepared to date and tested for biological activity all but one, Meshnick, S. R. et al (1984) Antimicrobal Agents Chemother. 25, 286–288, are conjugates of platinum(II) dichlorides. See: Alcock, H. R. et al (1976) J. Chem. Soc. Chem. Comm., 717; Carraher, C. E. et al (1984) Polym. Mater. Sci. Eng. 49, 210214 and 51, 307–311; Hurwitz, E. et al (1982) JNCI 69, 47–51 and EPO No. 99,133; De Clerq, E. et al (1983) Biochem. Biophys. Acta. 741, 358–363; and Takahaski, K. et al (1985) Jpn. J. Cancer Res. (Gann) 76, 68–74. As such, they readily form active platinum-(aquo)$_n$ species which accounts for the observed cytotoxicity, but bind ligand quickly and sometimes irreversibly upon formation.

In addition to binding serum proteins, platinum-(aquo)$_n$ species can oligomerize monoclonal antibody. Not only is drug stability highly questionable in these conjugates, but the incompatibility of drug with targeting agent makes these platinum(II)-containing carriers poorly suited for targeted chemotherapy. The only conjugate which does not contain Pt(II) dichlorides is a highly crosslinked platinum(II) dicarboxylate, and as such is not only poorly characterizable but probably highly immunogenic. To date very little effort has thus been made to design and control the chemistry of attaching antitumor platinum compounds to carrier macromolecules.

SUMMARY OF THE INVENTION

It is an object of the present invention to provide a method of detecting, localizing and/or treating a tumor or metastases with a platinum-containing composition.

It is another object of the present invention to provide a method of modifying carrier macromolecules with the drug platinum such that (i) the drug-carrier conjugate is water-soluble after the modification procedure and (ii) release of an "active" platinum antitumor complex from the carrier is possible.

A further object of the invention is to provide a method of targeting the platinum containing carrier to tumor cells.

It is another object of the invention to provide a method for detecting and localizing the targeting agent and/or platinum complex in vivo.

Further objects and advantages of the present invention will be apparent from the following detailed description of species thereof.

The objects of the present invention are achieved by linking an intact functionalized platinum complex to a bio-degradable, nonimmunogenic and nontoxic carrier molecule. The platinum complex is linked directly to the carrier molecule or indirectly through a ligand. The ligand in turn is linked directly or through spacer molecules to the carrier. Spacer molecules may be compounds susceptible to enzymatic cleavage. The platinum-carrier complex is linked directly or indirectly via a spacer or linker molecule to a targeting agent such as a monoclonal antibody. The resulting composition may be radiolabeled by any one of several procedures.

DESCRIPTION OF THE PREFERRED EMBODIMENT

The carrier macromolecule may be a polymer, biopolymer, polysaccharide, or protein of any molecular weight but advantageously a water-soluble molecule of 5 to 160 kilodaltons such as a dextran or inulin, albumin or other protein, or a polyaminoacid. Desirable characteristics of drug carrier systems have been summarized. See: Arnold, L. J. Jr. 1985, Methods in Enzymology, 112A, Widder, K. J. and Green, R. eds. 270–285, Molteni, L. ibid, 285–298; Bodmer, J. L. and Dean, R. T. ibid, 298–306 Sezaki, H. and Hashida, M. in Directed Drug Delivery (1985) Borchardt, R. T., Repta, A. J., and Stella, V. J., eds., 189–208; Duncan, R. and Kopecek, J. (1984) Adv. Polym. Sci. 57, 51–101.

In general, the macromolecular carrier should be biodegradable or at least should not exhibit deleterious cumulative effects. In addition, the macromolecular carrier and its metabolic degradation products should be nonimmunogenic and nontoxic. The drug-carrier conjugate should meet normal and reasonable criteria for pharmaceutical formulation such as purity, solubility, and stability sufficient to allow for human use.

The attachment of platinum drugs to macromolecular carriers may result in one or more of the following: (i) stabilization of the drug, (ii) increased solubility, (iii) retention in the circulatory system or vesicles, (iv) sustained or controlled release, and/or (v) diminished exposure of the drug to "non-target" tissues. The carrier may either redirect, intensify, or modulate drug activity, or it may simply reduce side effects of the parent drug.

If the platinum-containing carrier complex is targeted by means of targeting agents such as monoclonal antibodies, antibody fragments, or any tumor-selective agent, the carrier would provide the distinct advantage of allowing a large number of drug molecules to be attached to the targeting agent while minimally compromising the ability of the targeting agent to localize at the tumor site. The equivalent modification of monoclonal antibody with monomeric drug, for example, would be irreversibly detrimental to the antibody, resulting in either precipitation or a significant loss of original immunospecificity. Through the use of targeted drug-carrier conjugates, cytotoxicity is concentrated in the vicinity of the tumor while minimizing contact of the drug with sensitive normal cells such as those of the gastrointestinal tract and bone marrow.

Platinum may be attached to the macromolecular carrier by either reacting an intact functionalized platinum complex with the carrier, which may or may not be activated by one of the many procedures for the activation of such carriers, Axen, R. et al (1967) Nature (London) 214, 1302-4; Nilsson, K. and Mosbach, K. (1981) Biochem. Biophys. Res. Commun. 102, 449-52, or by first reacting the carrier with an appropriate ligand which can then serve to coordinate platinum in a subsequent reaction. In either of these ways, platinum may be attached to the carrier in a $+2$ or $+4$ oxidation state such that (i) linkage of the ligand to the carrier is covalent, (ii) the drug-carrier conjugate remains water-soluble after the modification procedure, and (iii) release of an "active" platinum antitumor complex from the carrier is possible.

The ligands may be mono- or bidentate in the case of amines or peptidic amines but are advantageously bidentate in the case of oxygen ligands such as malonates, glycolates, succinates, aspartates, etc., and are monodentate in the case of chlorides, hydroxides, etc. The ligands may either be attached directly to the carrier or through spacer molecules which in turn may be cleavable or non-cleavable in vivo by enzymatic, hydrolytic, or photolytic processes. The use of spacer molecules is advantageous in the case of covalent attachment to the carrier through the amine ligand(s), such as in an amide or ester of 2,3-diaminopropionic acid. Particularly useful are spacer molecules such as peptides and esters which are susceptible to cleavage by cathepsins, peptidases, esterases etc. present in tumor cells or on the surface of tumor cells which can aid in the release of drugs from the carrier molecule. See: Hjelle, J. T. et al J. Pharmacol. Exp. Ther. (1984) 229, 372-380; Barrett, A. J. and Kirschke, H. Methods in Enzymology (1981) 80, 535-561 and DeDuve, C. et al, Biochem. Pharmacol. (1974), 23, 2495-2531.

Direct linkage of the ligand to the carrier typically involves reaction between an appropriately functionalized ligand such as amino-malonic acid, and a carrier, such as a dextran or inulin which has been appropriately activated. If activated by sodium meta-periodate, then the reaction will be performed in the presence of a reducing agent such as sodium cyanoborohydride. The use of tritiated sodium borohydride here would allow for the introduction of a radiolabel. No such reduction would be necessary if the polyhydroxylic carrier were to be activated by cyanogen bromide or tresyl chloride. Dialysis and subsequent reaction at or near pH 6.0 with a diamine platinum diaquo species, such as that formed from the corresponding dichloride or diiodide upon treatment with aqueous silver nitrate, followed by dialysis and lyophilization will produce a platinum-containing carrier which is characterizable, water-soluble, stable, and suitable for (i) administration as a sustained-release formulation or (ii) targeting by any of the targeting agents previously described. See: Dhara, S. C. Indian J. Chem. (1970) 8, 193.

Indirect linkage of the ligand to the carrier typically involves the use of a ligand containing the appropriate side chain functionality, such as $\beta$-alanine tartronic ester or alanyl-leucyl-alanyl-leucyl-aminomalonic acid, with platinum as described above, to allow for (i) covalent coupling to the carrier, and (ii) enhanced release of platinum from the carrier. Peptides such as AlaLeuAlaLeu can be cleaved by cellular enzymes and have been shown to enhance drug release from carriers and targeting agents. See: Trouet, A. et al Proc. Natl. Acad. Sci. USA (1982) 79, 626-629.

Linkage of the platinum-containing carrier to the targeting agent may also be direct or indirect. Direct linkage typically involves reaction, for example, between residual aldehydes of a platinum-malonato dextran prepared by a periodate procedure, and amine moieties of the targeting agent, such as lysine residues, in the presence of a reducing agent such as sodium cyanoborohydride in aqueous buffer. Indirect linkage typically involves the use of a spacer or linker molecule on either the carrier or targeting agent or both. The addition of one to five percent of a cross-coupling agent, such as 3-maleimidopropionyl hydrazine, during the reaction of an aminomalonic acid with an activated dextran will specifically introduce a linker capable of coupling to the targeting agent through sulfhydryl groups which are naturally present or which can be chemically introduced by reagents such as 2-iminothiolane. See: Jue, R. et al (1978) Biochemistry, 17, 5399-5405. The reaction conditions for the above described attachments to targeting agent are such that (i) the binding specificity of the targeting agent, such as monoclonal antibody, active fragments thereof, or any tumor-selective agent, is retained after coupling with the platinum-containing carrier, (ii) the conjugate formed between the targeting agent and platinum-containing carrier remains soluble under physiological conditions, and (iii) the conjugate can be localized in vivo.

As will be appreciated, the targeting agent localizes the platinum-containing carrier on the surface of tumor cells where, in the case of non-modulating receptors, there is extracellular release of the antitumor platinum species contributing to a high localized concentration of the drug in the vicinity of the tumor. In the case of modulating receptors, the conjugate is internalized where intracellular release causes tumor cell death.

The platinum-containing carrier may be radiolabeled by (i) the use of tritiated sodium borohydride as described above, (ii) the use of Pt195 in the chemical synthesis of the platinum complex, or (iii) the addition of some percentage of a chemical compound, such as tyramine or tyrosine, during reaction of the ligand with the activated carrier, which can be radioiodinated prior to platination by any one of several procedures for the radioiodination of proteins. See: Greenwood, F. C. et al (1963), Biochem. J., 89, 114–116 with modifications by McConahey et al (1969) Int. Arch. Allergy Appen. Immunol. 29, 185.

Invention is illustrated by the following examples:

EXAMPLE 1

Pt-Malonato Dextran (Method A)

Dextran (2 g, $4.93 \times 10^{-5}$ mol, MW avg.=40,600) was oxidized by sodium meta-periodate (2.12 g, $9.93 \times 10^{-3}$ mol) in 0.1M acetate buffer, pH 5.6 overnight at ambient temperature in an effort to oxidize 80% of the sugar residues present in this dextran (201/252). Diethyl amino-malonate hydrochloride (4.19 g, $1.98 \times 10^{-2}$ mol) was saponified with 1N sodium hydroxide (61.4 ml) by stirring overnight at ambient temperature while the dextran dialyzed against water. Aqueous aminomalonic acid, adjusted to pH 6.5 with phosphoric acid, was added to the dialyzed dextran with stirring. Sodium cyanoborohydride ($9.93 \times 10^{-3}$ mol) was also added and stirring continued overnight at ambient temperature.

Cisplatin (5.94 g, $1.98 \times 10^{-2}$ mol) and silver nitrate (6.76 g, $3.98 \times 10^{-2}$ mol) were allowed to react in water (25 ml) overnight at ambient temperature in the dark, then filtered through diatomaceous earth. The dextran, dialyzed again and now modified with malonic acid residues, was adjusted to pH 6.0 with nitric acid and combined with the platinum solution, also adjusted to pH 6.0 with 1N sodium hydroxide. The reaction was stirred overnight at ambient temperature while protected from light, then dialyzed against water and lyophilized. Elemental analysis: C 27.18, H 5.08, N 7.24, Pt 28.30. $^{195}$Pt NMR ($\delta$, $D_{20}$): 1873 (br) ppm. IR (KBr): 1610–1660 (br) cm$^{-1}$. In vitro cytotoxicity testing: See Table 1. Pt release data: See Table 2.

EXAMPLE 2

Pt-Malonato Dextran (Method B)

Diethyl aminomalonate hydrochloride (1.42 g, $6.72 \times 10^{-3}$ mol) was added to 1N sodium hydroxide (25 ml) and stirred overnight at ambient temperature. Dextran (1 g, MW avg.=35,600) was dissolved in water (100 ml) and the pH adjusted to 10.7 with 1N sodium hydroxide. Cyanogen bromide (475 mg, $4.48 \times 10^{-3}$ mol) was added in two portions while maintaining the pH with 1N sodium hydroxide. After stirring for 1 hour, the pH was lowered to 9.0 with 1N hydrochloric acid. The aminomalonic acid solution prepared above was then added dropwise while maintaining the pH at 9.0 with 1N hydrochloric acid. After stirring at ambient temperature overnight, the mixture was dialyzed against water ($2 \times 2000$ ml), aq. sodium bicarbonate pH 9.0 ($2 \times 2000$ ml), and finally water ($1 \times 2000$ ml).

Cisdiiododiaminoplatinum(II) (2.1 g, $4.25 \times 10^{-3}$ mol) and silver nitrate (1.41 g, $8.32 \times 10^{-3}$ mol) were combined in water (50 ml), stirred for 3 hours in the dark, then filtered through diatomaceous earth. The filtrate was added to the dialyzed dextran solution with concurrent addition of 1N sodium hydroxide to maintain the pH at 6.0. The reaction was stirred for 16 hours while protected from light then dialyzed against water ($5 \times 2000$ ml) and lyophilized to give 1 g of a beige fluffy solid. ICP analysis indicated 16.3% Pt (w/w). Elemental analysis: C 30.37, H 5.25, N 4.93. In vitro cytotoxicity testing and lifespan summary: See Table 1. Pt release data: See Table 3.

EXAMPLE 3

Preparation of Antibody—Pt Malonato Dextran Conjugates

Dextran (MW=15–20K) was modified as described in Example 1. The ratio of aminomalonic acid used to oxidized residues was 0.5:1. Analysis showed that this preparation had 25.2 moles of platinum per mole of dextran and a final average molecular weight of approximately 31,500. Found: C 27.65%, H 4.42%, N 5.36%, Pt 18.8%. Pt release data: See Table 4.

Monoclonal antibody G 26.3 (5 mg, $3.2 \times 10^{-8}$ mol) at 2.24 mg/ml in 0.1M phosphate buffer, pH 8.0, was mixed with the Pt-malonato dextran described above. Sodium cyanoborohydride ($3.2 \times 10^{-7}$ mol) was added and the reaction stirred overnight at ambient temperature. The conjugate was purified by gel chromatography to give two fractions. Both the higher molecular weight fraction (MW avg.>190,000) and the lower molecular weight fraction (MW avg.=187,000) were found to have an antibody to Pt-malonato dextran ratio of 1:1 by protein (Bradford) and platinum (ICP) analyses. Testing of both fractions for binding to appropriate tumor lines showed retention of saturable binding by both fractions with only a slightly reduced binding constant. This demonstrated that the polymer-antibody complex is a stable targetable entity.

EXAMPLE 4

Pt-Malonato Dextran (with ester linker)

Dextran (0.5 g, MW=35,600) was oxidized with sodium metal-periodate (0.53 g), dialyzed into water (20 ml) and reacted with $\beta$-alanine tartronic ester, $H_2NCH_2CH_2CO_2CH(CO_2H)_2$, (575 mg, 3 mmol) in the presence of sodium cyanoborohydride (194 mg, 3.08 mmol) at pH 6.5 as described in Example 1. Dialysis against water and subsequent reaction with the diaquo species derived from cisplatin (0.9 g, 3 mmol) and silver nitrate (1 g, 5.88 mmol) afforded, after dialysis and lyophilization, the title compound which was found to contain 13.9% platinum by weight as per ICP analysis. Elemental analysis: C 31.04, H 4.91, N 4.52. Pt release data: See Table 5.

EXAMPLE 5

Pt-Isoserinato Dextran

Diaminocyclohexanedichloroplatinum(II) (3.76 g, $9.89 \times 10^{-3}$ mol) was reacted with silver sulfate (3.02 g, $9.69 \times 10^{-3}$ mol) in water (50 ml) with stirring in the dark for 24 hours at ambient temperature then filtered through diatomaceous earth. The filtrate was reacted with barium hydroxide (1.66 g, $9.69 \times 10^{-3}$ mol) by stirring for 24 hours in the dark at ambient temperature and was filtered.

Dextran (2 g, MW avg.=35,600) was dissolved in 0.2M acetate buffer, pH 5.6, (100 ml) and to it was added sodium meta-periodate (2.12 g, $9.9 \times 10^{-3}$ mol).

After stirring overnight in the dark at ambient temperature, the reaction was dialyzed against water then reacted with DL-isoserine (1 g, $9.51 \times 10^{-3}$ mol) and sodium cyanoborohydride (620 mg, $9.87 \times 10^{-3}$ mol). After stirring overnight at ambient temperature, the reaction was dialyzed against water and reacted with the platinum solution prepared, as described above, for 3 days in the dark. Dialysis and lyophilization afforded slightly over 1 g of a beige powder which was shown to contain 19% platinum (w/w) by ICP analysis. Elemental analysis: C 30.80, H 5.07, N 5.11. IR (KBr): 3350 (br), 2890, 2840, 1580 (br), 1010 $cm^{-1}$. Pt release data: See Table 6.

EXAMPLE 6

Pt-Aspartato Inulin

Cisplatin (3.65 g, $12.16 \times 10^{-3}$ mol) was reacted with silver nitrate (4.05 g, $23.83 \times 10^{-3}$ mol) in water (50 ml) for 24 hours in the dark with stirring at ambient temperature then filtered through diatomaceous earth.

Inulin (2 g, MW avg.=5,000) was reacted with sodium metaperiodate (2.6 g, $12.16 \times 10^{-3}$ mol) in water (100 ml) overnight with stirring at ambient temperature in the dark, then dialyzed against water, and reacted with L-aspartic acid (1.62 g, $12.16 \times 10^{-3}$ mol) and sodium cyanoborohydride (764 mg, $12.16 \times 10^{-3}$ mol) for 24 hours with stirring at ambient temperature at pH 6.5–7.5. The reaction was then dialyzed against water and reacted with the platinum solution prepared above at pH 6.0. After stirring 24 hours at ambient temperature in the dark, the reaction was dialyzed against water and lyophilized to afford 1.94 g of a white powder found to contain 22.7% Pt (w/w) by ICP analysis. Elemental analysis: C 23.95, H 3.99, N 6.35, IR (KBr): 3380 (br), 2910, 1580 (br), 1380, 1100, 1050 $cm^{-1}$.

EXAMPLE 7

Pt-Malonato Inulin

Inulin (2 g, MW avg.=5000) was oxidized as described in Example 6 and reacted with aminomalonic acid, prepared from diethyl aminomalonate hydrochloride (2.57 g, $12.16 \times 10^{-3}$ mol) and 1N sodium hydroxide (37.7 ml), and sodium cyanoborohydride (764 mg, $12.16 \times 10^{-3}$ mol) then dialyzed into water.

Cisplatin (3.65 g, $12.16 \times 10^{-3}$ mol) was reacted with silver nitrate (4.05 g, $23.83 \times 10^{-3}$ mol) in water (75 ml) then filtered and combined with the inulin solution described above.

Dialysis and lyophilization produced a beige powder found to contain 16.5% platinum (w/w) by ICP analysis. Elemental analysis: C 25.42, H 4.49, N 6.45. Pt release data: See Table 7.

EXAMPLE 8

Antibody Pt-malonato Inulin Conjugates

Monoclonal antibody 2H7 (7.5 mg, $4.8 \times 10^{-8}$ mol) at 5.48 L mg/ml in 0.1M phosphate buffer pH 8.0 was reacted with the Pt-malonato inulin (4 mg) described in Example 7, and sodium cyanoborohydride ($4.82 \times 10^{-7}$ mol) at ambient temperature for 20 hours with stirring. The reaction was then dialyzed against 0.1M phosphate buffer pH 7.4 and purified by gel chromatography to give two conjugate fractions. The higher molecular weight fraction (MW avg.>180,000, 42%) was found to contain 42 platinums per antibody while the lower molecular weight fraction (MW avg.=175,500, 58%) was found to contain 27.8 platinum per antibody molecule as verified by protein (Bradford) and platinum (ICP) analysis.

EXAMPLE 9

Pt-Malonato Xylan

Xylan (2 g, MW=10–20K) was reacted with sodium metaperiodate (2.59 g, $12.1 \times 10^{-3}$ mol) in 0.2M acetate buffer, pH 5.6, as previously described, then dialyzed and reacted with aminomalonic acid ($15.13 \times 10^{-3}$ mol) and sodium cyanoborohydride to afford a white powder (2.08 g). Elemental analysis: C 35.04, H 4.99, N 3.27. IR (KBr): 3400 (br), 2940, 1600 (br), 1320, 1040 $cm^{-1}$.

Cisplatin (3.63 g, $12.1 \times 10^{-3}$ mol) was reacted with silver nitrate (4.03 g, $23.7 \times 10^{-}$mol) in water (50 ml) for 24 hours with stirring in the dark at ambient temperature then filtered through diatomaceous earth, and combined with the xylan described above. Stirring for 24 hours in the dark at ambient temperature followed by dialysis and lyophilization afforded 1.98 g of a beige powder found to contain 36% platinum (w/w) by ICP analysis. Elemental analysis: C 21.35, H 3.94, N 8.22. IR (KBr): 3400 (br), 3260 (br), 2940, 1680 (br), 1370 (br), 1040 (br), $cm^{-1}$. Pt release data: See Table 8.

EXAMPLE 10

Pt-Glycolato-Dextran

Sodium meta-periodate (2.12 g, 9.9 mmol) was added to dextran (2 g, MW avg.=35,600) in 0.1M acetate buffer (20 ml, pH 5.6), stirred 6 hours at room temperature, then exhaustively dialyzed against water (Spectrapor membrane MW cutoff 12–14K).

To the aqueous solution containing periodate-oxidized dextran was added sodium cyanide (971.5 mg, 19.8 mmol) and $CaCl_2$ (1.22 g, 11 mmol). The mixture was stirred 24 hours at room temperature, 24 hours at 50° C. where ammonia evolution was more pronounced, cooled, filtered, then dialyzed against water and lyophilized to give 340 mg of a slightly colored water-soluble powder. IR (KBr): 3380 (br), 2920, 1720, 1580, 1400, 1020 $cm^{-1}$.

To diaminocyclohexanedichloroplatinum(II) (711 mg, 1.87 mmol) in water (5 ml) was added silver sulfate (560 mg, 1.8 mmol) with stirring. After 24 hours at room temperature in the dark, the mixture was filtered through diatomaceous earth, and to the filtrate was added barium hydroxide (307 mg, 1.8 mmol) with stirring. After 24 hours at room temperature, in the dark, the mixture was filtered, the filtrate added to the glycolato dextran (335 mg) in water (5 ml). After stirring 24 hours while protected from light, the mixture was allowed to stand 48 hours in the dark, then dialyzed exhaustively against water, and lyophilized. ICP analysis indicated 22.2% platinum by weight.

EXAMPLE 11

Pt-Malonato Dextran (with peptide linker)

Diethyl alaleualaleu-aminomalonate (0.9 g, 1.39 mmole) was added to 0.5N sodium hydroxide (8 ml) and stirred at room temperature for 16 hours. The pH of the solution was adjusted to 6.8 with dilute nitric acid.

Dextran (1.0 g; MW 35,600) was activated by oxidation with sodium meta-periodate (1.92 g, 4.38 mmole) in 0.2M sodium acetate, pH 5.6, at room temperature for 16 hours while protected from light. The reaction mixture was dialyzed repeatedly against water ($6 \times 1000$ ml). Following dialysis, the pH of the solution was adjusted to 6.8 with 0.5N NaOH.

The peptide-dextran coupling was performed by the slow addition of the peptide solution to the dextran solution, followed by stirring at room temperature for 2 hours, and subsequent addition of sodium cyanoborohydride (0.117 g, 1.82 mmole). The reaction mixture was stirred at room temperature for 16 hours then dialyzed repeatedly against water (6×2000 ml).

Coupling efficiency was determined by lyophilization of an aliquot of the above reaction mixture and elemental analyses of the isolated white solid: C 29.64, H 4.62, N 6.38. Coupling efficiency 61%.

Cis-diamino diaquo platinum(II) was prepared by addition of silver nitrate (0.55 g, 3.24 mmole) to a stirred mixture of cis-diamino dichloroplatinum(II) (0.5 g, 1.66 mmole). The reaction mixture was stirred at room temperature for 16 hours while protected from light and filtered through diatomaceous earth. The final pH of the solution was adjusted to 6.0 with 1N sodium hydroxide.

The platination of the peptide-dextran conjugate was performed by the dropwise addition of the cis-diamino diaquo platinum solution to the dextran solution while maintaining the pH at 6.0 with concurrent addition of 1N sodium hydroxide. Following addition, the reaction mixture was stirred at room temperature for 16 hours while protected from light. Subsequent dialysis against water (6×2000 ml) and lyophilization afforded a white flaky solid (0.32 g). ICP analysis indicated 12.8% platinum by weight.

TABLE 1

IN-VITRO CYTOTOXICITY TESTING[1]

| Compound and Vehicle | IC$_{50}$ (ug/ml)/Active Dilution | | | |
|---|---|---|---|---|
| | A549 | B16-F10 | HCT-116 | SW1271 |
| Pt—malonato Dextran Method A saline | >500 | 426 | >500 | 408 |
| Pt—malonato Dextran Method B saline | N.T. | 332 | 430 | >500 |

[1] Cell lines:
A549 — Human lung
B16-F10 — Murine melanoma
HCT-116 — Human colon
SW1271 — Human lung
N.T. — Not tested

Effect on L1210 Leukemia[2]

| Compound and Vehicle | mg/kg/dose or dilution | Rt., schedule | Med. S.T. | % T/C | AWG Gm D.5 | No. mice alive/tot D.5 |
|---|---|---|---|---|---|---|
| Pt—malonato Dextran, Method B | 160 | i.p., Q01DX1;1 | 7.5 | 107 | 1.0 | 4/4 |
| H$_2$O + tween 80 | 120 | | 7.0 | 100 | 2.7 | 4/4 |
| | 80 | | 7.0 | 100 | 2.1 | 4/4 |
| Cisplatin BS | 10 | i.p., Q01DX1;1 | 12.0 | 171 | −2.4 | 6/6 |
| | 8 | | 9.5 | 136 | −1.4 | 6/6 |
| | 6 | | 11.0 | 157 | −0.9 | 6/6 |
| | 4 | | 9.0 | 129 | 0.2 | 6/6 |

[2] Implant level: 1 × 10$^6$ cells
Site: i.p.
Treatment: 21 days after implant

LIFESPAN SUMMARY[3]

| Compound and Vehicle | mg/kg/dose or dilution | Rt., schedule | Med. S.T. | % T/C | AWG Gm D.5 | No. mice alive/tot D.5 |
|---|---|---|---|---|---|---|
| Pt—malonato Dextran, Method B | 400 | i.p., Q01DX1;1 | 10.0 | 143 | −4.5 | 4/4 |
| H$_2$O + tween 80 | 320 | | 8.0 | 114 | −4.3 | 4/4 |
| | 240 | | 8.5 | 121 | −4.6 | 4/4 |
| | 160 | | 7.5 | 107 | −2.4 | 4/4 |
| Cisplatin BS | 10 | i.p., Q01DX1;1 | 12.0 | 171 | −3.3 | 6/6 |
| | 8 | | 12.0 | 171 | −2.8 | 6/6 |
| | 6 | | 11.0 | 157 | −2.1 | 6/6 |
| | 4 | | 9.0 | 129 | −0.7 | 6/6 |

[3] Tumor: L1210
Day: 14

TABLE 2

| pH | Time (h) | | | |
|---|---|---|---|---|
| | 2 | 24 | 48 | 72 |
| 5.60 | 0.6 | 4.3 | 6.8 | 8.2 |
| 6.80 | 0.5 | 6.6 | 10.2 | 13.3 |
| 8.30 | 1.3 | 7.2 | 10.3 | 13.8 |

TABLE 3

| pH | Time (h) | | | |
|---|---|---|---|---|
| | 2 | 24 | 48 | 72 |
| 5.52 | 5.3 | 17.8 | 26.8 | 27.0 |
| 6.86 | 3.9 | 18.3 | 22.0 | 24.0 |
| 8.20 | 3.7 | 11.7 | 16.2 | 17.4 |

TABLE 4

| pH | Time (h) | | | |
|---|---|---|---|---|
| | 1 | 16 | 40 | 64 |
| 5.50 | 0.6 | 5.2 | 6.4 | 7.6 |
| 7.10 | 0.6 | 4.2 | 4.9 | 6.1 |
| 8.20 | 0.7 | 4.2 | 5.1 | 6.4 |

TABLE 5

| pH | Time (h) | | | | |
|---|---|---|---|---|---|
| | 2 | 18 | 42 | 66 | 138 |
| 5.37 | 4.1 | 25.0 | 37.8 | 45.2 | 61.5 |
| 6.67 | 2.6 | 21.5 | 33.1 | 42.0 | 55.8 |
| 7.81 | 2.8 | 21.0 | 34.7 | 43.5 | 59.1 |

TABLE 6

| pH | Time (h) | | | |
|---|---|---|---|---|
| | 1 | 24 | 48 | 120 |
| 5.80 | 9.5 | 72.5 | 88.5 | 98.7 |
| 7.00 | 8.8 | 61.1 | 76.3 | 89.3 |
| 8.00 | 8.8 | 55.7 | 66.9 | 76.2 |

*0.1M phosphate buffer

TABLE 7

| pH | Time (h) | | | | |
|---|---|---|---|---|---|
| | 1 | 24 | 48 | 72 | 144 |
| 5.42 | 4.7 | 18.1 | 20.5 | 26.2 | 27.5 |
| 6.76 | 3.1 | 15.2 | 18.3 | 20.0 | 22.7 |
| 7.86 | 4.9 | 17.8 | 21.0 | 21.9 | 28.8 |

TABLE 8

| pH | Time (h) | | | | |
|---|---|---|---|---|---|
| | 1 | 24 | 48 | 72 | 144 |
| 5.80 | 3.1 | 22.6 | 29.8 | 32.8 | 41.9 |
| 7.00 | 2.1 | 17.9 | 23.7 | 27.5 | 40.9 |
| 8.00 | 1.7 | 18.9 | 25.4 | 28.2 | 35.8 |

*0.1M phosphate buffer

It will be appreciated by those skilled in the art that various other modifications are contemplated according to and implied by the invention.

What is claimed is:

1. A composition comprising a pharmaceutically acceptable polysaccharide carrier which has been chemically activated by oxidation and then linked to platinum in either a +2 or +4 oxidation state through a bidentate oxygen containing ligand including an amine group which is coupled to the oxidized group of the activated polysaccharide.

2. A composition according to claim 1 wherein said ligand and said carrier molecule are linked together through a spacer molecule.

3. A composition according to claim 2 wherein said spacer molecule may be cleaved in vivo.

4. A composition according to claim 1 wherein said platinum-containing macromolecule is linked to a targeting molecule.

5. A composition according to claim 4 wherein said platinum-containing macromolecule is linked to said targeting molecule through a spacer molecule.

6. A composition according to claim 4 wherein said targeting molecule is a monoclonal antibody or a fragment of a monoclonal antibody.

7. A composition according to claim 1 wherein said composition is radiolabeled so that tumor cells are treated and/or localized.

8. A composition as claimed in claim 1 wherein said composition is a sustained or controlled release formulation.

9. A method of detecting, localizing and/or treating a tumor or metastases which comprises administering a composition according to claim 1.

10. A composition according to claim 1 wherein the polysaccharide is activated by oxidation to provide aldehyde groups for binding to the amine group of the bidentate oxygen ligand.

11. A composition according to claim 10 which is water-soluble and wherein the polysaccharide is dextran, the dextran is activated by treatment with sodium periodate, and the platinum is linked to the dextran through a ligand derived from an amino malonic acid.

* * * * *